(12) United States Patent
Ma et al.

(10) Patent No.: US 12,305,222 B2
(45) Date of Patent: May 20, 2025

(54) METHOD FOR IDENTIFYING WHETHER A DIPLOID POTATO IS SELF-COMPATIBLE

(71) Applicant: YUNNAN NORMAL UNIVERSITY, Kunming (CN)

(72) Inventors: Ling Ma, Kunming (CN); Yi Shang, Kunming (CN); Sanwen Huang, Kunming (CN); Chunzhi Zhang, Kunming (CN); Dongli Gao, Kunming (CN)

(73) Assignee: YUNNAN NORMAL UNIVERSITY, Kunming (CN)

( * ) Notice: Subject to any disclaimer, the term of this patent is extended or adjusted under 35 U.S.C. 154(b) by 1 day.

(21) Appl. No.: 17/831,546

(22) Filed: Jun. 3, 2022

(65) Prior Publication Data

US 2022/0298549 A1 Sep. 22, 2022

Related U.S. Application Data (63) Continuation of application No. PCT/CN2020/094886, filed on Jun. 8, 2020.

(30) Foreign Application Priority Data

Dec. 4, 2019 (CN) .......................... 201911230000.X (51) Int. Cl.
| | | |
|---|---|---|
| *C12Q 1/6809* | (2018.01) | |
| *A01H 1/04* | (2006.01) | |
| *A01H 5/06* | (2018.01) | |
| *A01H 6/82* | (2018.01) | |
| *C07K 14/415* | (2006.01) | |
| *C12Q 1/6858* | (2018.01) | |
| *C12Q 1/6895* | (2018.01) | |
| *G16B 30/00* | (2019.01) | |

(52) U.S. Cl.
CPC .......... *C12Q 1/6809* (2013.01); *A01H 1/045* (2021.01); *A01H 5/06* (2013.01); *A01H 6/827* (2018.05); *C07K 14/415* (2013.01); *C12Q 1/6858* (2013.01); *C12Q 1/6895* (2013.01); *G16B 30/00* (2019.02); *C12Q 2600/13* (2013.01); *C12Q 2600/156* (2013.01); *C12Q 2600/158* (2013.01)

(58) Field of Classification Search
None
See application file for complete search history.

(56) References Cited

FOREIGN PATENT DOCUMENTS

| CN | 107619873 A | 1/2018 |
|---|---|---|
| CN | 108849471 A | 11/2018 |
| CN | 110894539 A | 3/2020 |
| CN | 110938120 A | 3/2020 |
| WO | 2011053135 A2 | 5/2011 |
| WO | 2012144902 A1 | 10/2012 |
| WO | 2020226499 A1 | 11/2020 |

OTHER PUBLICATIONS

NIH National Cancer Institute, Definition of genotyping—NCI Dictionary of Genetics Terms—NCI (cancer.gov) (2024) (Year: 2024).*
Collard et al., An introduction to markers, quantitative trait loci (QTL) mapping and marker-assisted selection for crop improvement: The basic concepts, 2005, vol. 142, pp. 169-196. (Year: 2005) (Year: 2005).*
Xun Xu et al., Genome sequence and analysis of the tuber crop potato, 2011, Nature, vol. 475, pp. 189-195. (Year: 2011) (Year: 2011).*
Hosaka et al., Genetics of self-compatibility in a self-incompatible wild diploid potato species Solanum chacoense. 2. Localization of an S locus inhibitor (Sli) gene on the potato genome using DNA markers, 1998, Euphytica, vol. 103, pp. 265-271 (Year: 1998).*
Barone, Amalia, 2004, Molecular marker-assisted selection for potato breeding, American Journal of Potato Research, vol. 81, pp. 111-117 (Year: 2004).*
John Innes Centre, 2019, https://www.jic.ac.uk/blog/what-is-genotyping/ (Year: 2019).*
Ma et al., 2022, Patent Application Publication US 2022/0298549 A1, published Sep. 22, 2022 (Year: 2022).*
Van Der Burgt et al., Patent Application Publication No. US 2022/0267386 A1, published on Aug. 25, 2022 (Year: 2022).*

(Continued)

*Primary Examiner* — Cathy Kingdon
*Assistant Examiner* — Christina L Meadows
(74) *Attorney, Agent, or Firm* — Flener IP & Business Law; Zareefa B. Flener (57) ABSTRACT

The present application relates to the technical field of genetic breeding, and provides a method for identifying whether a diploid potato is self-compatible. The method relates to identifying whether a StSCI gene in the diploid potato is transcribed and expressed. Also disclosed is a method for identifying whether a StSCI gene is expressed by using molecular marker, and a method of screening for the molecular marker, which includes: obtaining the genome sequence information of parental materials, screening for difference sites of the parental materials, screening for the molecular marker, and identifying whether the screened molecular marker are usable. As for the identification of the self-compatibility of a diploid potato by using the screened molecular marker, the identification workload is small, a lot of time is saved, and the identification result is not affected by the environment, and it is accurate and reliable.

6 Claims, 1 Drawing Sheet

Specification includes a Sequence Listing.

(56) References Cited

OTHER PUBLICATIONS

Enciso-Rodriguez et al., 2019, Overcoming self-incompatibility in diploid potato using CRISPR-CAS9, Frontiers in Plant Science, vol. 10(376), pp. 1-12 (Year: 2019).*
Manrique-Carpintero et al., Genetic Map and QTL Analysis of Agronomic Traits in a Diploid Potato Population using Single Nucleotide Polymorphism Markers, 2015, Crop Science, vol. 55, pp. 2566-2579 (Year: 2015).*
European Patent Office, Communication Pursuant to Rule 114(2) EPC, Third Party Observation for EP20200895309, dated Apr. 11, 2022.
Xinwei Chen, et al. Title of the article: Identification and rapid mapping of a gene conferring broad spectrum late plight resistance in the diploid potato species Solanum verrucosum through DNA capture technologies, Theoretical and Applied Genetics, vol. 131 1287-1297, Published Mar. 18, 2018.
Felix Enciso-Rodriguez, et al. Title of the article: Overcoming Self-Incompatibility in Diploid Potato Using CRISPR-Cas9, Frontiers in Plant Science, vol. 10 1-12, Published Apr. 2, 2019.
Brenda A. Peterson, et al. Title of the article: Self-Fertility in a Cultivated Diploid Potato Population Examined with the Infinium 8303 Potato Single-Nucleotide Polymorphism Array, The Plant Genome, vol. 9 1-13 Published Nov. 2016.
Linham Sun, et al. Title of the article: S-Locus F-Box Proteins Are Solely Responsible for S-RNase-Based Self-Incompatibility of Petunia Pollen, The Plant Cell, vol. 30 2959-2972 Published Dec. 2018.
Title of the article: SubNameFull= F-box protein PP2-B10 {Eco: 0000313EnsemblPlants: PGSC0003DMT400043434}, Published Apr. 3, 2013.
Wang Pei, Title of the article: Establishment and preliminary study of the diploid inbred lines of potato, Chapter 2 pp. D047-307, Published Apr. 30, 2016.
PCT Written Opinion of the International Searching Authority, International application No. PCT/CN2020/094886, Sep. 15, 2020.
International Search Report, International application No. PCT/CN2020/094886, Sep. 15, 2020.
European search report, Application No./Patent No. 20895165.7-1118 / 4023771 PCT/CN202009488, Sep. 30, 2022.
The State Intellectual Property Office of People's Republic of China, Application No. or Publication No. 201911230000. K, First Office Action, Dec. 4, 2019.
Kazuyoshi Hosaka & Robert E. Hanneman, Genetics of self-compatibility in a self-incompatible wild diploid potato species *Solanum chacoense*.2.Localization of an S locus inhibitor(Sli)gene on the potato genome using DNA markers, Euphytica, 1998, pp. 265-271, vol. 103, Netherlands.
Ma, et al., A nonS-locus F-box gene breaks self-incompatibility in diploid potatoes, Nature Communications, Jul. 6, 2021, pp. 1-8, vol. 12, published Online.
R. K. Birhman and K. Hosaka, Production of inbred progenies of diploid potatoes using an S-locus inhibitor(Sli) gene, and their characterization, Genome, May 11, 2000, pp. 495-502, vol. 43, Canada.
Eggers, et al., Neofunctionalisation of the Sli gene leads to self-compatibility and facilitates precision breeding in potato, Nature Communications, Jul. 6, 2021, pp. 1-9, vol. 12, published Online.
Alignment 1: SEQ ID No. 2 Maps To 'M6 High Confidence Gene MODELS-cDNA'G26388.TL WITH 97% Sequence Identity; Internet Database-Potato Genomics Resource; Online.
Alignment 2: SEQ ID No. 6 Maps To M6_V4.1_SCAFFOLD_421:32630-33167 With 100% Sequence Identity; Internet Database—Potato Genomics Resource; Online.
Alingment 3: SEQ ID No. 3 Maps To M6_V4.1_SCAFFOLD_421:31276-33275 With 100% Sequence Identity; Internet Database-Potato Genomics Resource; Online.
Translation 4: SEQ ID No. 2 Encodes a Non-Functional Protein; Internet Database-Potato Genomics Resource; Online.
S.H. Jansky, et al.; M6: A Diploid Potato Inbred Line for Use in Breeding and Genetics Research; Journal of Plant Registrations-Germplasm; Feb. 21, 2014; pp. 195-199; vol. 8(2); USA.
Courtney P. Leisner, et al.; Genome sequence of M6, a diploid inbred clone of the hig-glycolkaloid-producing tuber-bearing potato species Solanum chacoense, reveals residual heterozygosity; The PLant Journal, 2018; pp. 562-570; vol. 94(3); England.
The Potato Genome Sequencing Consortium; Genome sequence and analysis of the tuber crop potato; Nature; Jul. 2011; pp. 189-195; vol. 475; England.
Chalermpol Phumichai, et al.; Toward the development of highly homozygous diploid potato lines using self-compatibility controlling Sli gene; Genome; Nov. 2025; pp. 977-984; vol. 48; Canada.
Kazuyoshi Hosaka and Rena Sanetomo; Creation of a highly homozygous diploid potato using the S locus inhibitor(Sli) gene; Euphytica; Oct. 7, 2020; pp. 1-16; vol. 216:169; Netherlands.
Communication Pursuant To Rule 114(2) EPC for Serial No. 20895309.1; issued Jul. 11, 2023.

* cited by examiner

SEQUENCE LISTING

<160> NUMBER OF SEQ ID NOS: 12

<210> SEQ ID NO 1
<211> LENGTH: 4289
<212> TYPE: DNA
<213> ORGANISM: Unknown
<220> FEATURE:
<223> OTHER INFORMATION: nucleotide sequence of the StSCI gene

<400> SEQUENCE: 1

| | | | | | |
|---|---|---|---|---|---|
| atctcgagtt | aatttcacat | ttgatcactg | aacttttccc | actataagtg | actacatgtt | 60 |
| atccactctt | aacactacgt | gcctcgacaa | ttttaggtga | aaagtctaaa | ttacttaact | 120 |
| tttctatct | tgcagatttc | cattgaaatc | ccatatgtct | ttatgcaatc | tgttttctgt | 180 |
| ggtgcaatta | tgtatgctat | gatcggattt | gaatggacgg | tagcaaagtt | cttttggtac | 240 |
| ttgttcttcc | tgttttcac | cctcttgtac | ttcactttct | acggtatgat | gaccgttgct | 300 |
| gttaccccaa | atgtaagtgt | tgctcaaatt | gtcggctcct | tcttctacgg | agtatggaat | 360 |
| cttttctcag | gattcatcat | tccacgaact | gtaagttctt | gaaacacttc | catttattg | 420 |
| ttacatcaaa | actgacttag | agctcggaaa | tgacatgttc | tctgtatttt | tttccatttt | 480 |
| catttttaaa | aaacagcgta | ttcccatatg | gtggagatgg | tactactggt | gttgtcctgt | 540 |
| tgcctggacc | ttgtatggtt | tggttgcatc | acaatttgga | gatcttcaga | acaaacttac | 600 |
| tgatgaggaa | acagtggaac | aattttttgag | acgttacttc | ggcttcaagc | atgattttct | 660 |
| tccaatagtt | gcagtcgcga | ttgttgggta | cactgttctt | tttggcttca | catttgcttt | 720 |
| cgctattaag | gcattcaact | tccaaacgag | ataaaaagac | attacctgct | gaagatgtag | 780 |
| taaagacaac | gtgtgaaacg | ttctctccac | tgctcgtgaa | atggggaaga | cgcggttagt | 840 |
| ataaggaatt | tttctcgagc | tcaagtacga | gcaagagatt | gattttgaaa | gtactgtata | 900 |
| tagattacca | cttgaacaag | ggtatgttct | gttattatta | ttatttttta | tgaatttcaa | 960 |
| gttcattttt | ctgtgtaaga | gatagtaatt | tgttaatgtt | gaagtactat | tctgttacta | 1020 |
| tctggtgttt | cttgtacttt | tgttgtgtct | ttttctgaac | tgctttggat | tattttctc | 1080 |
| gagtcgagga | tctatcggaa | gaagactttc | tacctctgag | gtaagagtaa | agtttgctta | 1140 |
| cactctaccc | ttcccatact | ccactttgtg | ggggagacac | atggtatgtt | gttcttatag | 1200 |
| ttacaactat | aagaaattaa | tgaaatgatg | aatgtaagaa | tttgtgaata | ttgcttttcg | 1260 |
| ggaactgcca | caactgtggt | gcgagaatga | gacttctcta | gtgttaacta | acaacaagt | 1320 |
| ctttggttg | aattcggaga | atggagaaat | tcttggtcgg | gaacgctcct | tgataaatgg | 1380 |
| accttagatg | atgctaatct | taaattagtc | gggccagtaa | atttcgaatc | ttccaagaca | 1440 |
| tttcatgttt | taattcacta | aaaaggaaag | acaaaaaatt | tcaaactcaa | aacatttcat | 1500 |
| gtttagtatt | attggaatat | cttcctccac | atgagttgtt | tgtttggtgt | atctaagcaa | 1560 |
| tatcaattct | ttaattttat | tttttttgg | aaataaaatg | tacatatgtg | agaactagat | 1620 |
| aaaaataatg | aaaaataaac | aaaaatgatt | tttttaaaaa | taaataaaa | ttaaatattt | 1680 |
| tcacttccat | taggccaaaa | gggtatatct | aggctatttg | tgtaatagta | taggtatgta | 1740 |
| tgagccattt | ttataacgag | gtatgtatca | gctctaaatt | atatgacctt | ttcacttatt | 1800 |
| atattcatac | tggagaagta | aaaatgaaca | aaacaatatt | taaccgcagt | gccggctcaa | 1860 |
| tgcttataaa | aattaggcat | atgccttagg | cccccaattt | taggggggcc | tcaaatttt | 1920 |
| accaacaata | aattatgtgt | taattttttt | tatagaaaaa | attaattatt | taagataaat | 1980 |
| gtacttttca | tatatatatt | atttttattct | ccttaacctc | aatcaaatag | aagaaatcaa | 2040 |

```
gaaaaacgtt gttttgtctt cttacactct cttcacttac tctcgcgttg taattttcta    2100 taccccttt atactctatg taagttagag ctctatcaaa aatatgaatc aatagtaaaa     2160
ctaatgtgtt ggataaagcg aattacaagc ctgtttagat tgacttatgt tatgtgcttt    2220
taaataaaaa aagaagttta taagcagttt tgtcaactta ttacttatag aataatgtta    2280
acaatttatt taataattgc ctcagctaaa agatttttagg cctttaattt aaattttgtt   2340
ttaggcctcc aaatacgttg agccgccct gcttaaccgt cgagacatat gaagtgtaac     2400
aacttttcaa caaactttc tcagtttgct ttatataaag aaaaaaaatt cacaaaactt     2460
caaattcaat tttccaataa tggactattt cctattgcta ccagaagatt gtgtttgtga    2520
tattctctcc tttacttccc cgaaagacgt cgtgatttca tccgcgatct ctcggggatt    2580
caactctgct gctgaatccg acgttatttg ggtaaagttt ttaccagatg attatgaaga    2640
tatcaactcg agatatgtct ccccgcggat ttatccgtct aaaaaggagc tttactttag    2700
tctatgtgac ttccctgttc taatggatgg aggcaaattg gtaagtagct ctaaattggg    2760
aagtagcaag ctttttcttt ggctcattag ttgaatatat gtataattgt tttgaagctt    2820
atgggttcgg gatttttttgt gtgttttttg agttgtttgg ttcgaaatta ataattttgtt  2880 acaaattaga ggagttttct ttttaaagat aaaatacaga gtttgaacta aaactattgg    2940
gttcctagaa tttatagggg tgttctagct ttgcctctaa ctgttggtgt tgtataacgg    3000
taaaggtcat gaacctttga cctgaggtct agagtttgag ttttaatcag agttgaaatc    3060
ttaggaattg agtcgtgttt aataggaagc actaaaatct actagtgtgc ttacggctgc    3120
gcaaatctta attaatcagc caatgaattt ttcttatttt attttgtttt tgttacaaac    3180
tgggaatcca actctctata gtaaaacgga agttcagata gtcaactaaa tgaacttcta    3240
agattttctg gccaatgggt tacaaacacc attaaaaatg caaaattaaa tagattataa    3300
taataattgt gtgaattta ttttattttt gaatggacta tatataagct agtagtgtga    3360
atctaagatt ttattttatt tttgaaaaca gagttttttca cttgataaga aaacaggcaa    3420 gaaatgttt atgatatcag ctagagaact tgctattaca tggggagttg atacaccatg     3480
gtattgggaa tggattctc atcctgactc caggttcgtc gaaaaattat actacatata    3540
aaaagttatt ctttttttt atgtatgtac tacgtataaa aaattatact tcattgcctt     3600
ttaacgaatt tctacatatg ttatttttg aatcccttgg ttgaaattct acctctgcca    3660
ctattggtga gaattttttt tttacacaat caagccacct aaaagatata tatagatgag    3720
cctcactaaa atgtgtaatg aaatatgtta cctattacaa taggtaaaga tgatttgatg    3780
gtgcaaaaat tacttatatt ggcgatgtta tatataactt aaactcacta aatacgtgta    3840
tctaagacaa tatagacatt ttattttgca gattttcgga agtggctcat ctcaagggtg    3900
taagttggct agacatacga ggcacgattg gaacacaaat attgtcgaaa agaaccaaat    3960
atgttgttta tttggtgttc aaattgtcaa agaatcatga tggactagaa attgctaatg    4020
catttgttag gtttgtgaat cgtgtgagcg acaaagaggc cgaggaacga gctagtgtcg    4080
tgagtctagt cggaaaaagg gttaggagac gcaaacgtaa tgtgaaatgt ccacgaaaaa    4140
gagtcgatga atggatggaa atagaattgg gaaatttat caatgataca ggagatgatg    4200
gagatgttga agcgcgattg atggagatta cgcagcttca tggaaaaggt ggccttattg    4260
ttcaaggaat tgaatttaga ccagaataa                                     4289
```

<210> SEQ ID NO 2

```
<211> LENGTH: 538
<212> TYPE: DNA
<213> ORGANISM: Unknown
<220> FEATURE:
<223> OTHER INFORMATION: nucleotide sequence of the inserted sequence

<400> SEQUENCE: 2
cagggggggc tcaacgtatt tggaggccta aacaaaatt taaattaaag gcctaaaatc     60
ttttagctga ggcaattatt aaataaattg ttaacattat tctataagta ataagttgac   120
aaaactgctt ataaacttct ttttttattt aaaagcacat aacataagtc aatctaaaca   180
ggcttgtaat tcgctttatc caacacatta gttttactat tgattcatat ttttgataga   240
gctctaactt acatagagta taaaaggggt atagaaaatt acaacgcgag agtaagtgaa   300
gagagtgtaa gaagacaaaa caacgttttt cttgatttct tctatttgat tgaggttaag   360
gagaataaaa taatatatat atgaaaagta catttatctt aaataattaa ttttttctat   420
aaaaaaaatt aacacataat ttattgttgg taaaaatttg aggccccccct aaaattgggg   480 gcctaaggca tatgcctaat tttataagc attgagccgg cactgcggtt aaatattg      538

<210> SEQ ID NO 3
<211> LENGTH: 101
<212> TYPE: DNA
<213> ORGANISM: Artificial Sequence
<220> FEATURE:
<223> OTHER INFORMATION: KASP primer sequence

<400> SEQUENCE: 3
ttatgatctt gataaactat atattatcaa tatgaatgtt gtaattgata tattattttg    60
aactttgtcc aatctatatt agttatttaa gtcatcatat t                      101

<210> SEQ ID NO 4
<211> LENGTH: 101
<212> TYPE: DNA
<213> ORGANISM: Artificial Sequence
<220> FEATURE:
<223> OTHER INFORMATION: KASP primer sequence

<400> SEQUENCE: 4
ttatgatctt gataaactat atattatcaa tatgaatgtt gtaattgata cattattttg    60
aactttgtcc aatctatatt agttatttaa gtcatcatat t                      101

<210> SEQ ID NO 5
<211> LENGTH: 20
<212> TYPE: DNA
<213> ORGANISM: Artificial Sequence
<220> FEATURE:
<223> OTHER INFORMATION: primer sequence

<400> SEQUENCE: 5
ggtgtatcga gtcggaataa                                                20

<210> SEQ ID NO 6
<211> LENGTH: 20
<212> TYPE: DNA
<213> ORGANISM: Artificial Sequence
<220> FEATURE:
<223> OTHER INFORMATION: primer sequence

<400> SEQUENCE: 6
gattcgggaa attgtactca                                                20
```

```
<210> SEQ ID NO 7
<211> LENGTH: 22
<212> TYPE: DNA
<213> ORGANISM: Artificial Sequence
<220> FEATURE:
<223> OTHER INFORMATION: the first forward primer 1F

<400> SEQUENCE: 7
cgtcggattc agcagcagag tt                                              22

<210> SEQ ID NO 8
<211> LENGTH: 27
<212> TYPE: DNA
<213> ORGANISM: Artificial Sequence
<220> FEATURE:
<223> OTHER INFORMATION: the first reverse primer 1R

<400> SEQUENCE: 8
tccacatgag ttgtttgttt ggtgtat                                         27

<210> SEQ ID NO 9
<211> LENGTH: 22
<212> TYPE: DNA
<213> ORGANISM: Artificial Sequence
<220> FEATURE:
<223> OTHER INFORMATION: the second forward primer 2F

<400> SEQUENCE: 9
cgtcggattc agcagcagag tt                                              22

<210> SEQ ID NO 10
<211> LENGTH: 29
<212> TYPE: DNA
<213> ORGANISM: Artificial Sequence
<220> FEATURE:
<223> OTHER INFORMATION: the second reverse primer 2R

<400> SEQUENCE: 10
aagcgaatta caagcctgtt tagattgac                                       29

<210> SEQ ID NO 11
<211> LENGTH: 29
<212> TYPE: DNA
<213> ORGANISM: Artificial Sequence
<220> FEATURE:
<223> OTHER INFORMATION: primer sequence

<400> SEQUENCE: 11
atcagctaga gaacttgcta tttcatggg                                       29

<210> SEQ ID NO 12
<211> LENGTH: 26
<212> TYPE: DNA
<213> ORGANISM: Artificial Sequence
<220> FEATURE:
<223> OTHER INFORMATION: primer sequence

<400> SEQUENCE: 12
cgtgcctcgt atgtctagcc aactta                                          26
```

METHOD FOR IDENTIFYING WHETHER A DIPLOID POTATO IS SELF-COMPATIBLE

CROSS-REFERENCE

This application is a continuation of International Application No. PCT/CN2020/094886, filed on Jun. 8, 2020, which claims priority to Chinese Patent Application No. 201911230000.X, filed on Dec. 4, 2019. The disclosures of the aforementioned applications are hereby incorporated by reference in their entireties.

TECHNICAL FIELD

This application relates to the technical field of genetic breeding, in particular to a method for identifying whether a diploid potato is self-compatible, a method of screening for molecular markers for identifying whether a diploid potato is self-compatible, a reagent, a kit and an identification method.

BACKGROUND

In the breeding process of diploid potatoes, diploid potatoes are usually self-incompatible. When pollen of itself or the same S haplotype of the plant falls on the stigma, the pollen tube cannot extend all the way to the ovule to complete the fertilization process. Therefore, pollen having the same S haplotype as its own cannot allow this diploid potato plant to produce seeds. In order to realize seed breeding in diploid potatoes, some researches are devoted to changing the self-incompatibility defect of a diploid potato through gene editing.

However, it is always difficult to identify a self-compatible diploid potato material. Currently, as for identifying the self-compatibility phenotype of a diploid potato plant, it requires the plant to grow to the full bloom stage, and its own pollen is used to conduct a large amount of pollination work. The self-compatibility of the plant is judged according to whether the plant sets fruits after pollination. However, the fruit setting of a plant is affected by many internal and external factors, for example, low pollen activity due to immature pollen development, high temperature or low temperature during pollination will affect plant fruit setting. As a flowering plant, potato may have hybrid fruit setting by cross-pollination between adjacent plants due to wind blowing or the tweezers are not cleaned during pollination. Thus the self-compatibility phenotype of a plant cannot be accurately represented by without fruit setting or few fruit setting of the plant in a single year. Repeated identification in multiple locations and multiple years is required. Therefore, the traditional method for identifying the self-compatibility phenotype is time-consuming, labor-intensive and inaccurate. There is an urgent need to develop a simple, rapid and accurate method for identifying the self-compatibility phenotype.

SUMMARY

In view of this, this application is dedicated to providing a method for identifying whether a diploid potato is self-compatible, generally identifying with molecular markers, and a method of screening for molecular markers for identifying whether a diploid potato is self-compatible. As for the identification of the self-compatibility of a diploid potato by using the screened molecular markers, the identification workload is small, a lot of time is saved, and the identification result is not affected by the environment, and it is accurate and reliable.

In one aspect of the application, provided is a method for identifying whether a diploid potato is self-compatible: identifying whether the StSCI gene in the diploid potato is transcribed and expressed.

Diploid potato material RH89-039-16 (see the article: Self-Fertility in a Cultivated Diploid Potato Population Examined with the Infinium 8303 Potato Single-Nucleotide Polymorphism Array) is self-compatible, the self-compatibility traits of the diploid potato material RH89-039-16 are controlled by a gene which is named as self-compatibility induction gene (SCI), abbreviated as StSCI gene.

It is found in studies that in the diploid potato material RH89-039-16, the StSCI gene is located on chromosome 12, and it is heterozygous on chromosome 12 of RH89-039-16. If the StSCI gene is expressed normally, the diploid potato material may change from self-incompatibility to self-compatibility. In most diploid potato materials, the promoter of StSCI gene lacks activity and cannot normally start the expression of StSCI gene. While in the diploid potato material RH89-039-16, the promoter region of StSCI gene is inserted a specific 538 bp fragment including a core promoter element, so that the promoter has the activity of promoting the expression of the StSCI gene, thereby expressing the StSCI gene in the pollen.

The protein encoded by the StSCI gene is called StSCI protein which may inhibit the cytotoxicity of a variety of S-RNases, thereby preventing S-RNase from degrading rRNA in the pollen tube and depolymerizing the cytoskeleton in the pollen tube, so as to reduce the damage of the pollen tube cell caused by S-RNase and ensure the normal extension of the pollen tube; thus the pollen tube may extend to the ovule to complete the fertilization process, thereby overcoming the self-incompatibility of the diploid potato material. Therefore, the diploid potato plant in which the StSCI gene is normally expressed is self-compatible.

Further, the nucleotide sequence of the StSCI gene includes or consists of the following sequence:
 1) the nucleotide sequence represented by SEQ ID NO: 1; or
 2) the complementary sequence, degenerate sequence or homologous sequence of the nucleotide sequence represented by SEQ ID NO: 1;

Preferably, the homologous sequence is a polynucleotide sequence having about 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more identity with the nucleotide sequence represented by SEQ ID NO: 1.

In one embodiment of the present application, the nucleotide sequence of the StSCI gene is the nucleotide sequence represented by SEQ ID NO: 1.

In one embodiment of the present application, the nucleotide sequence of the StSCI gene is the complementary sequence of the nucleotide sequence represented by SEQ ID NO: 1. The complementary sequence is a nucleotide sequence which is able to hybridize with the nucleotide sequence of SEQ ID NO: 1 under stringent conditions.

Exemplarily, the "stringent conditions" refer to conditions under which a probe will hybridize to its target sequence to a detectable extent beyond hybridization with other sequences (such as at least 2 times the background). Stringent conditions are sequence-dependent, and vary from different environments. By controlling the stringency of hybridization and/or washing conditions, a target sequence that is 100% complementary to the probe may be identified. Alternatively, stringent conditions may be adjusted to allow some sequence mismatches, so that a lower degree of similarity is detected.

In one embodiment of the present application, the nucleotide sequence of the StSCI gene is a degenerate sequence of the nucleotide sequence represented by SEQ ID NO: 1. A degenerate sequence means that after changing one or more nucleotides in the nucleotide sequence of SEQ ID NO: 1, the position of the changed nucleotide(s) in this sequence corresponds to the same type of the encoded amino acid, and thus it will not affect the function and expression level of the StSCI gene.

In an embodiment of the present application, the nucleotide sequence of the StSCI gene is a homologous sequence of the nucleotide sequence represented by SEQ ID NO: 1. The homologous sequence include, but is not limited to, a polynucleotide sequence having about 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more identity with the nucleotide sequence represented by SEQ ID NO: 1.

Further, the presence of a molecular marker is used to predict whether the StSCI gene is expressed.

Further, a method of screening for molecular markers for identifying whether a diploid potato is self-compatible, including the following steps:
(a) obtaining the genome sequence information of the parent materials:
by utilizing the self-compatible diploid potato RH89-039-16 and the self-incompatible diploid potato as parent materials, re-sequencing the genome of RH89-039-16 and the self-incompatible diploid potato to obtain the genome sequence information; or
developing corresponding primers according to the sequence information of the reference genome, performing PCR amplification on the target gene fragment of the parent materials, and sequencing the amplified products to obtain the sequence information of the specific fragment of the parent materials.

It should be noted that, the types of the self-incompatible diploid potatoes are not specifically limited. Potato materials satisfying self-incompatibility and being diploid may be used in this application.

Further, the types of the self-incompatible diploid potatoes may be, but are not limited to, PI 225689, DM1-3 516 R44, *Solanum Chacoense*, and S15-65. The preferred self-incompatible diploid potato is PI 225689.

In this application, the diploid potato material RH89-039-16 with self-compatibility is used as a parent to hybridize with the self-incompatible diploid potato to obtain hybrid offspring, thereby transferring the nucleotide sequence for controlling the self-compatibility of RH89-039-16 into the hybrid offspring of the diploid potatoes through genetic recombination, so as to construct a self-compatible plant line with excellent traits of both parents.

At this time, the parent materials RH89-039-16 and the self-incompatible diploid potato are re-sequenced to find the sequence differences between the two parents. Not only may it be used to study the reason for the self-compatibility of RH89-039-16, but also may it be used to develop molecular markers for identifying the self-compatibility traits of a diploid potato through genomic differences.

Alternatively, through primer amplification, PCR amplification is performed on the target chromosome fragment of the parent materials, and the amplified products are sequenced to obtain the sequence information of the specific fragment of the parent materials, and molecular markers for identifying the self-compatibility traits of a diploid potato is developed by comparing the difference of the sequence information of the specific fragment in the two parent materials.

(b) Screening for the difference sites of the parental materials:
comparing the sequence information of the two parent materials RH89-039-16 and the self-incompatible diploid potato, and screening out the difference site of the nucleotide sequence of the StSCI gene and/or the nucleotide sequence of the StSCI gene linkage; wherein the difference sites of the nucleotide sequence include: single-base difference sites and/or InDel markers.

It should be noted that, "analyzing the nucleotide sequence of the StSCI gene and/or the nucleotide sequence of the StSCI gene linkage" represents three analysis ways: (1) analyzing the nucleotide sequence of the StSCI gene; (2) analyzing the nucleotide sequence of the StSCI gene linkage; (3) analyzing the nucleotide sequence of the StSCI gene and the nucleotide sequence of the StSCI gene linkage.

In one embodiment of this application, the genome sequences of two parent materials RH89-039-16 and PI 225689 are analyzed, and the single-base difference sites between RH89-039-16 and PI 225689 are screened out by analyzing the nucleotide sequence of the StSCI gene.

In one embodiment of this application, the genome sequences of two parent materials RH89-039-16 and PI 225689 are analyzed, and the InDel markers between RH89-039-16 and PI 225689 are screened out by analyzing the nucleotide sequence of the StSCI gene.

In one embodiment of this application, the genome sequences of two parent materials RH89-039-16 and PI 225689 are analyzed, and the single-base difference sites between RH89-039-16 and PI 225689 are screened out by analyzing the nucleotide sequence of the StSCI gene linkage.

In one embodiment of this application, the genome sequences of two parent materials RH89-039-16 and PI 225689 are analyzed, and the InDel markers between RH89-039-16 and PI 225689 are screened out by analyzing the nucleotide sequence of the StSCI gene linkage.

(c) Screening for the molecular markers:
designing primer sequences of KASP markers for the single-base difference site selected in step (b); and/or designing primer sequences of InDel markers for the InDel markers selected in step (b).

In one embodiment of the present application, the method for designing the primer sequences of the KASP markers is: to reserve n bases in the upstream and downstream of the different single base sequence, and then design a primer sequence of 2n+1 bases including different single base therebetween, wherein, for example, n may be 3-100, 5-80, 20-90, 30-80, 40-70, or 50-60.

In one embodiment of the present application, the method for designing the primer sequences of the InDel markers is: to design suitable primer fragments in the upstream and downstream having the InDel sites, and design a suitable primer pair; due to the change in the number of bases in this sequence, after using a primer pair to amplify the base sequence including the InDel sites by PCR, then identifying by using polyacrylamide gel electrophoresis (PAGE electrophoresis), and the difference in bands may be observed.

(d) Identifying whether the developed molecular markers are usable:

identifying whether the genome sequencing results of the molecular markers screened in step (c) are identical to those of the RH89-039-16 and the self-incompatible diploid potato parent materials, as well as the hybrid offspring of the RH89-039-16 and the self-incompatible diploid potato, and if the results are identical, the molecular markers are usable.

In one embodiment of the present application, when the screened KASP molecular markers are used to identify whether the diploid potatoes of the hybrid offspring of RH89-039-16 and the self-incompatible diploid potato are self-compatible, analyzing the KASP results by alignment, so as to determine the presence or absence of a single-base difference site in the genome of the hybrid offspring, whether the single-base difference site is identical to RH89-039-16, or identical to the self-incompatible diploid potato, thereby determining whether the hybrid offspring are self-compatible.

In one embodiment of the present application, when the screened InDel markers are used to identify whether the diploid potatoes of the hybrid offspring of RH89-039-16 and the self-incompatible diploid potato are self-compatible, analyzing the differences in the bands of the PCR products after electrophoresis by alignment, so as to determine whether an InDel site is included in the genome of the hybrid offspring, thereby determining whether the hybrid offspring are self-compatible.

Further, in the step (b), the genetic distance of gene linkage is less than 20 cM.

When analyzing the discrepancy sequence in the genome of the parent materials RH89-039-16 and the self-incompatible diploid potato, not only may the discrepancy sequence be found mainly in the nucleotide sequence of the StSCI gene, but also the discrepancy sequence may be found in the nucleotide sequence of the StSCI gene linkage in which the genetic distance is less than 20 cM. Due to linkage inheritance, the discrepancy sequences in the nucleotide sequence of the StSCI gene and the StSCI gene linkage will enter the offspring through gene recombination at the same time. The molecular markers developed on the basis of the found discrepancy sequences may be used to identify whether the hybrid offspring of the parents are self-compatible.

The genetic distance of gene linkage includes but is not limited to: 1 cM, 2 cM, 3 cM, 4 cM, 5 CM, 6 CM, 7 CM, 8 CM, 9 CM, 10 cM, 11 cM, 12 cM, 13 cM, 14 cM, 15 CM, 16 cM, 17 cM, 18 cM, 19 cM, 19.5 cM, or 19.9 cM.

The smaller the genetic distance of gene linkage and the higher the linkage strength, the lower the frequency of exchange. If the genetic distance between the developed molecular marker and the StSCI gene is 20 cM, then there is a 20% genetic exchange rate when the molecular markers are used to identify the self-compatibility of the offspring, and the degree of accuracy for identifying the self-compatibility of the offspring is 60-80%, i.e., after identifying 100 diploid potato plants, the identification results of 60-80 plants are accurate.

Further preferably, the genetic distance of gene linkage in the step (b) is less than 10 cM.

The genetic distance of gene linkage includes but is not limited to: 1 cM, 2 cM, 3 cM, 4 cM, 5 CM, 6 CM, 7 CM, 8 CM, 9 CM, 9.5 cM or 9.9 cM.

It is preferable to reduce the genetic distance between the developed molecular marker and the StSCI gene, which may further improve the accuracy for identifying the molecular marker. If the genetic distance between the developed molecular marker and the StSCI gene is 10 cM, then there is a 10% genetic exchange rate when the molecular markers are used to identify the self-compatibility of the offspring, and the degree of accuracy for identifying the self-compatibility of the offspring is 80-90%, i.e., after identifying 100 diploid potato plants, the identification results of 80-90 plants are accurate.

Further, in the step (b), through analyzing the nucleotide sequence of the StSCI gene and/or the nucleotide sequence of the StSCI gene linkage, screening out the RH89-039-16 in which the promoter region of the StSCI gene is inserted a nucleotide sequence fragment as compared with the self-incompatible diploid potato, wherein the nucleotide sequence fragment includes or consists of the following sequence:

1) the nucleotide sequence represented by SEQ ID NO: 2; or
2) a functional homologous sequence having at least 90% sequence identity with the nucleotide sequence represented by SEQ ID NO: 2; or,
3) a polynucleotide hybridizing to the nucleotide sequence represented by SEQ ID NO: 2 under stringent conditions.

The promoter is a DNA sequence fragment recognized, bound and started transcription by RNA polymerase, and it includes conserved sequences required for RNA polymerase specific binding and transcription initiation; most of the conserved sequences are located upstream of the transcription initiation point of structural genes, and the promoter itself is not transcribed. The sequence length of the promoter cannot be accurately determined, as long as the promoter includes the core promoter fragment, it may allow the StSCI gene to express.

In one embodiment of the present application, the nucleotide sequence of the inserted sequence is the nucleotide sequence represented by SEQ ID NO: 2.

In an embodiment of the present application, the nucleotide sequence of the inserted sequence is a functional homologous sequence having at least 90% sequence identity with the nucleotide sequence represented by SEQ ID NO: 2.

Preferably, wherein the homologous sequence is a polynucleotide sequence having about 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more identity with the nucleotide sequence represented by SEQ ID NO: 2.

In one embodiment of the present application, the nucleotide sequence of the inserted sequence is a polynucleotide hybridizing with the nucleotide sequence represented by SEQ ID NO: 2 under stringent conditions.

Exemplarily, the "stringent conditions" refer to conditions under which a probe will hybridize to its target sequence to a detectable extent beyond hybridization with other sequences (such as at least 2 times the background). Stringent conditions are sequence-dependent, and vary from different environments. By controlling the stringency of hybridization and/or washing conditions, a target sequence that is 100% complementary to the probe may be identified. Alternatively, stringent conditions may be adjusted to allow some sequence mismatches, so that a lower degree of similarity is detected.

Another aspect of this application provides molecular markers obtained by the above method of screening for molecular markers for identifying whether a diploid potato is self-compatible.

Molecular markers include, but are not limited to, one or a combination of more selected from the group consisting of: KASP marker, InDel marker, RFLP marker, RAPD marker, SSR marker, SSLP marker, AFLP marker, STS marker, or EST marker.

In one embodiment of the present application, the molecular marker is KASP molecular marker.

KASP molecular markers can be used to detect the single-base difference sites in the hybrid offspring of the diploid potatoes, and the corresponding KASP molecular markers may be developed for multiple single-base difference sites at the same time. Additionally, quick detection of the differences may also improve the accuracy of identification.

In one embodiment of the present application, the molecular markers are InDel molecular markers.

InDel molecular markers can be used to detect the InDels in the hybrid offspring of the diploid potatoes. Whether the hybrid offspring includes InDels is determined on the basis of the band difference of PCR products of the InDel molecular marker primers after electrophoresis, the detection results are relatively straightforward, and the accuracy of identification is high.

KASP marker primers and InDel marker primers may be used alone or in combination.

Another aspect of the present application provides a reagent including the above molecular marker.

The specific type of the above reagent is not limited, as long as it includes the above molecular marker, such as but not limited to KASP molecular marker, and InDel molecular marker. The above reagent may be used to identify whether a diploid potatoes is self-compatible.

Another aspect of the application provides a kit including the molecular marker or the reagent.

The specific type of the kit is not limited, but it needs to include the above molecular marker, or the above reagent, and may also include other components, such as PCR polymerase, buffer, dNTPs, and the like. The kit may be used to identify whether a diploid potatoes is self-compatible.

Another aspect of this application provides a method for identifying whether a diploid potato is self-compatible, including identifying whether the diploid potato is self-compatible by using the above molecular marker, or the above reagent, or the above kit.

Whether a diploid potato is self-compatible may be determined by identifying the specific nucleotide sequences in the genome of the diploid potato (such as whether it includes single-base difference sites or InDels), and whether the StSCI gene in the diploid potato plant to be tested is in a homozygous expression state or a heterozygous expression state may also be determined by the identification results of the nucleotide sequences. This method may be used to determine whether the self-compatibility phenotype of the offspring will segregate, which is of great significance to the selection of self-compatible parents in breeding. The traditional identification methods do not have such ability.

Using molecular markers for identification, the genome of diploid potatoes may be extracted at the seedling stage to perform this identification. There is no need for diploid potatoes to grow to the full bloom stage to observe whether they may be self-pollinated and determine whether they are self-compatible. The workload is small, and a lot of time is saved. Moreover, the identification result obtained by using molecular markers is not affected by the environment, and is accurate and reliable.

In an embodiment of the present application, the method for identifying whether a diploid potato is self-compatible includes the following steps:
(i) performing hybridization by using self-compatible diploid potato RH89-039-16 and self-incompatible diploid potato PI 225689 as the parent materials to obtain the hybrid offspring of the diploid potatoes;
(ii) extracting the leaf genome when the hybrid offspring plants grow to the seedling stage;
(iii) identifying the leaf genome by the molecular markers, and determining whether the hybrid offspring of the diploid potatoes are self-compatible according to the identification results of the molecular markers.

In an embodiment of the present application, the method for identifying whether a diploid potato is self-compatible includes the following steps:
(i) performing hybridization by using self-compatible diploid potato RH89-039-16 and self-incompatible diploid potato PI 225689 as the parent materials to obtain the hybrid offspring of the diploid potatoes;
(ii) extracting RNA from the plant cells of the hybrid offspring of the diploid potatoes, detecting whether the StSCI gene mRNA itself or its characteristic fragments exist in the plant cells of the hybrid offspring of the diploid potatoes by PCR method.

This method may be used to directly detect whether the StSCI gene in the hybrid potato plants is transcribed into mRNA, and it is accurate, fast and simple.

Compared with the traditional method for identifying the self-compatibility phenotype, the above technical solution adopted in this application has the following beneficial effects:
(1) in this application, the molecular markers are used to identify whether a diploid potato is self-compatible, the genome of the diploid potato may be extracted at the seedling stage for identification; it is no need to identify whether the diploid potato is self-compatible by traditional method until the diploid potato plants grow to the full bloom stage; the workload is small, and a lot of time is saved;
(2) in this application, the molecular markers are used for identification, and the identification result is obtained directly by detecting the genome of the samples, thus the identification result is not affected by the environment, and it is accurate and reliable;
(3) in this application, the homozygous status of the StSCI gene in the diploid potato plant to be tested may be determined by the identification results of the molecular markers, thereby determining whether the self-compatibility phenotype of the offspring will segregate, which is of great significance for selecting the self-compatible parents in breeding.

DETAILED DESCRIPTION OF EMBODIMENTS

The technical solutions in the Examples of the present application will be clearly and completely described below, with reference to the drawings in the Examples of the present application. Obviously, the described examples are only a part of the examples of the present application, rather than all the examples. Based on the examples in this application, all other examples obtained by those of ordinary skill in the art without creative work shall fall within the protection scope of this application.

Definition

The term "self-compatibility" refers to the ability to produce seeds through self-pollination and self-fertilization, and the seeds may grow into fertile offspring and produce seeds.

As used herein, the term "diploid" refers to that each vegetative cell in a plant includes two sets of chromosomes (2x-2n, where n is the number of chromosomes). A set of chromosomes is provided by two parents.

As used herein, the term "gene" refers to a genetic unit (usually represented by a DNA sequence) occupying a specific location in a chromosome and including genetic instructions that contribute to the potential phenotypic characteristics or traits of a plant.

As used herein, the term "hybridization" refers to using male plants (or gametes) to fertilize female plants (or gametes). The term "gamete" refers to a haploid germ cell (egg or sperm) involved in sexual reproduction produced in a plant by gametophyte mitosis, wherein the two heterosexual gametes fuse to form a diploid zygote during sexual reproduction process. This term generally refers to pollen (including sperm cells) and ovules (including egg cells). Therefore, "hybridization" usually refers to fertilizing an individual's ovule with the pollen of another individual.

The term "recombination" refers to the exchange of information between two homologous chromosomes during meiosis. In a "recombinant" plant, DNA originally present at a specific location within the chromosome (for example, linked to a gene/site) is exchanged with DNA from another plant (i.e., exchanging between female parent and male parent or vice versa).

The term "single-abase difference site", i.e., single nucleotide polymorphism (SNP), refers to the difference site of a single nucleotide (base) at the genomic level existing in two parents.

The term "KASP marker", KASP is the abbreviation of Kompetitive Allele Specific PCR.

The term "KASP marker primer" is a primer designed and developed for a single-base difference site.

The term "insertion-deletion marker", i.e. InDel (insertion-deletion), refers to the difference in the genome between the two parents. Compared with the other parent, a certain number of nucleotide insertions or deletions exist in the genome of one parent.

The term "InDel marker primer" refers to a PCR primer designed to amplify the InDel sites according to these InDel sites in the genome.

Example 1

A method for identifying whether a diploid potato is self-compatible, including the following steps:

(1) Re-sequencing the genomes of the parental materials RH89-039-16 and PI 225689:

RH89-039-16 is a self-compatible potato diploid material, and PI 225689 is a self-incompatible diploid potato material; after using these two materials as the parents for hybridization, the offspring have segregated traits of self-compatibility and self-incompatibility. In order to accurately identify the self-compatibility phenotype of the offspring, the parent materials RH89-039-16 and PI 225689 are re-sequenced to obtain the sequence information of the two materials.

(2) Developing molecular markers co-segregating with StSCI gene in parent materials RH89-039-16 and PI 225689:

After comparing the sequence information of the chromosome fragments including the StSCI gene in the parent materials RH89-039-16 and PI 225689, it is found that a 538 bp (SEQ ID NO: 2) nucleotide sequence has been inserted into the promoter region of the StSCI gene in RH89-039-16. A pair of InDel molecular markers are designed according to this inserted sequence, and the primer sequences are as follows:

F:
(SEQ ID NO: 9)
5'-CGTCGGATTCAGCAGCAGAGTT-3';

R:
(SEQ ID NO: 10)
5'-AAGCGAATTACAAGCCTGTTTAGATTGAC-3'.

(3) Identifying the phenotype of hybrid offspring plants by using InDel molecular markers:

When the hybrid offspring plants grow to the seedling stage, the leaf genome is extracted for PCR amplification reaction by using the primers in step (2), and the genomic DNA to be tested is used as a template.

A 20 µl amplification system is used in the PCR reaction: 1 µl of 10-20 ng/µl template DNA, 1 µl of 10 pmol/µl primers F and R respectively, 0.4 µl of 10 mmol/L dNTP mix, 0.3 µl of 0.5U/µL Taq DNA polymerase, 2 µl of 10×PCR reaction buffer, and the rest is water.

PCR reaction conditions are: 94° C. for 5 min; 94° C. for 20 sec, 55° C. for 20 sec, 72° C. for 30 sec, 35 cycles; 72° C. for 10 min.

Figure 1:
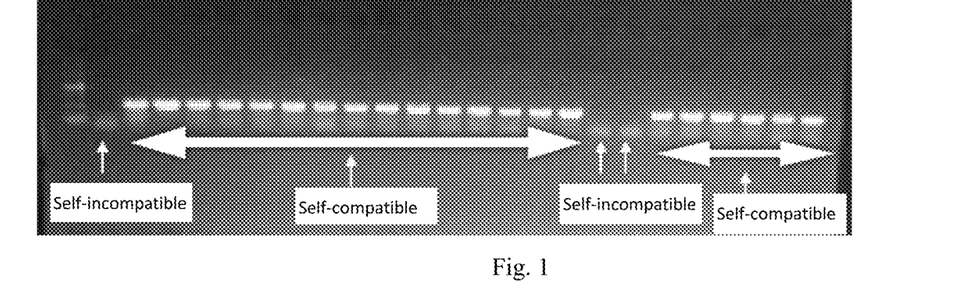
FIG. 1 is an agarose gel electrophoresis detection figure of the PCR reaction product in Example 1.

The PCR reaction product is detected by agarose gel electrophoresis, and the results are shown in FIG. 1. If the fragment of 428 bp may be amplified, then it indicates that the individual plant is self-compatible; if the fragment cannot be amplified, then it indicates that the individual plant is self-incompatible.

Figure 2:
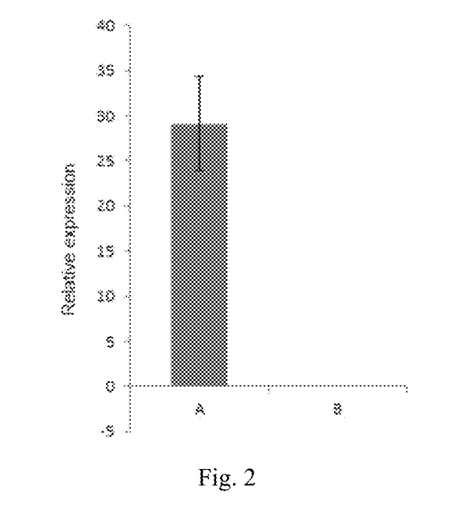
FIG. 2 shows the expressions of StSCI gene in individual plants A and B in Example 1.

(4) Identifying the expression of StSCI gene in individual offspring plant by quantitative PCR:

In order to verify the expression of the StSCI gene in the self-compatible individual plant identified by molecular markers, as for the hybrid offspring when the individual hybrid plant A which is identified as self-incompatible and the individual hybrid plant B which is identified as self-incompatible by molecular markers grow to full flowering stage, the pollen of the plants is removed out by tweezers, and the total RNA in the pollen and leaves is extracted by using a total RNA extraction kit (Cat. No. DP419) from Tiangen Biotech Co. Ltd.@ according to the operation instructions, conducting reverse transcription by using TaKaRa Reverse Kit (Cat. No. RR047A) to obtain cDNA, then detecting the expression of StSCI gene by qRT-PCR with the TaKaRa Quantitative Kit (Cat. No. RR820A) according to the operation instructions. The results of the quantitative detection are shown in FIG. 2.

The primer sequences of the quantitative detection are as follows:

```
F:
                                    (SEQ ID NO: 11)
5'-ATCAGCTAGAGAACTTGCTATTTCATGGG-3';

R:
                                    (SEQ ID NO: 12)
5'-CGTGCCTCGTATGTCTAGCCAACTTA-3'.
```

Reverse transcription reaction system and the conditions:

Reaction for removing the genomic DNA: 2 μl of 5×gDNA Eraser Buffer, 1 μl of gDNA Eraser, 1 μl of total RNA (1 μg/μl), 6 μl of RNase Free ddH20, 42° C. for 2 min.

Reverse transcription reaction: 10 μl product of the reaction for removing genomic DNA, 1 μl of PrimeScript RT Enzyme Mix I, 1 μl of RT Prime Mix, 4 μl of 5×PrimeScript Buffer2, 4 μl of RNase Free ddH20, 37° C. for 15 min, 85° C. for 5 sec.

Quantitative reaction system and the conditions:

20 μl of system for the quantitative PCR reaction: 10 μl of TB Green Premix Ex Taq II, 0.8 μl of PCR Forward Primer, 0.8 μl of PCR Reverse Primer, 0.4 μl of ROX Reference Dye, 2 μl of DNA template, and 6 μl of RNase Free ddH20.

Reaction conditions: 95° C. for 30 sec; 95° C. for 5 sec, 60° C. for 30 sec, 40 cycles; 95° C. for 15 sec, 60° C. for 1 min, 95° C. for 15 sec.

It may be seen from the results in FIG. 2 that, in the pollen of the self-compatible individual plant A, the StSCI gene may be expressed; while in the self-incompatible individual plant B, the StSCI gene is not expressed.

Figure 3:
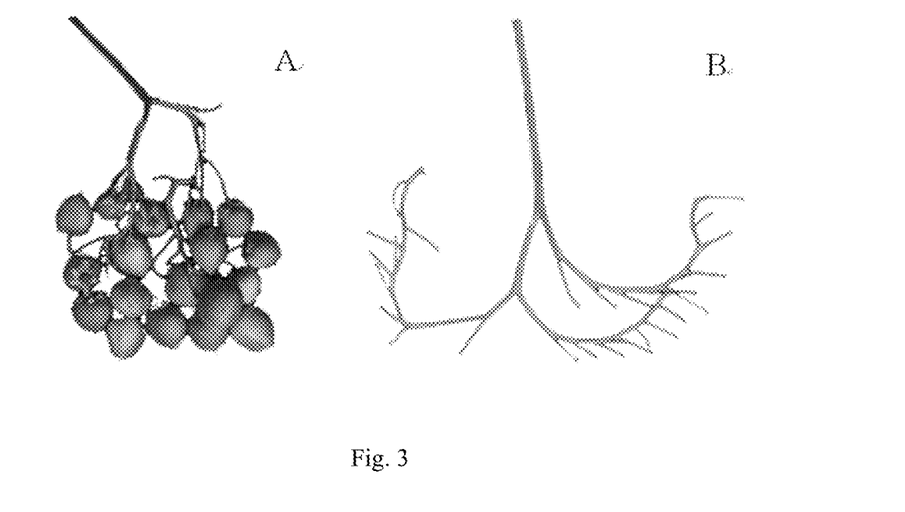
FIG. 3 shows the identification of the self-compatibility phenotype of the hybrid offspring in Example 1.

(5) Identifying the self-compatibility phenotype:

The self-compatible individual plant A and the self-incompatible individual plant B are routinely self-pollinated, and the fruit setting after pollination is observed. The results are shown in FIG. 3. After self-pollination, the fruits of the self-compatible individual plant A may develop normally, however the flowers of the self-incompatible individual plant B are withered with no fruit setting.

Example 2

A method of screening for molecular markers for identifying whether a diploid potato is self-compatible, including the following steps:

(1) Obtaining the genome sequence information of the parent materials:

Self-compatible diploid potato RH89-039-16 and self-incompatible diploid potato PI 225689 are used as parent materials to perform hybridization to obtain hybrid offspring, re-sequencing the genome of RH89-039-16 and PI 225689 to obtain the genome sequence information.

(2) Screening for the single-base difference sites of the parental materials:

The nucleotide sequence of the StSCI gene and the nucleotide sequence of the StSCI gene linkage are analyzed and screened to find that, a T base is located at 58030614 bp on chromosome 12 of RH89-039-16, while a C base is located at the corresponding position on the PI 225689 material.

The StSCI gene has a nucleotide sequence represented by SEQ ID NO: 1; the genetic distance of gene linkage is less than 20 cM.

(3) Designing KASP molecular markers:

50 bp of base sequence is retained respectively in the upstream and downstream of the different single base sequence, and a total of 101 bp of KASP primer sequence is designed including the different single base in the middle; the primer sequence is:

```
TTATGATCTTGATAAACTATATATTATCAATATGAATGTTGTAATTGATA

[T:C]ATTATTTTGAACTTTGTCCAATCTATATTAGTTATTTAAGTCATC

ATATT, (SEQ ID NO: 3) and (SEQ ID NO: 4); [T:C]

position is the SNP site at position 58030614;
```

(4) Identifying whether the screened molecular markers are usable:

The screened KASP molecular markers are identified whether they are identical to the genome sequencing results of RH89-039-16 and PI 225689 parent materials, and the test results show that they are identical. The KASP molecular markers may be used for subsequent identification.

Example 3

A method of screening for molecular markers for identifying whether a diploid potato is self-compatible, including the following steps:

(1) Obtaining the genome sequence information of the parent materials:

Self-compatible diploid potato RH89-039-16 and self-incompatible diploid potato PI 225689 are used as parent materials to perform hybridization to obtain hybrid offspring, re-sequencing the genome of RH89-039-16 and PI 225689 to obtain the genome sequence information.

(2) Screening for the InDel markers of the parental materials:

The nucleotide sequence of the StSCI gene and the nucleotide sequence of the StSCI gene linkage are analyzed to screen out that an 11 bp nucleotide sequence is missing at position 58136285 in chromosome 12 of RH89-039-16 as compared with PI 225689.

The StSCI gene has a nucleotide sequence represented by SEQ ID NO: 1; and the genetic distance of gene linkage is less than 20 cM.

(3) Designing the InDel molecular markers:

An appropriate primer fragment is designed respectively upstream and downstream of the InDel site, and primers for amplifying a total of 108 bp fragment including the 11 bp missing sequence are designed. The primer sequences at both ends are as follows:

```
F:
                                    (SEQ ID NO: 5)
5'-GGTGTATCGAGTCGGAATAA-3';

R:
                                    (SEQ ID NO: 6)
5'-GATTCGGGAAATTGTACTCA-3'.
```

(4) Identifying whether the screened molecular markers are usable:

The screened InDel molecular markers are identified whether they are identical to the genome sequencing results of RH89-039-16 and PI 225689 parent materials, and the test results show that they are identical. The InDel molecular markers may be used for subsequent identification.

Example 4

A method of screening for molecular markers for identifying whether a diploid potato is self-compatible, including the following steps:

(1) Sequencing the genome of parent materials RH89-039-16 and C:

Self-compatible diploid potato RH89-039-16 and self-incompatible diploid potato PI 225689 are used as parent materials to perform hybridization to obtain hybrid offspring, re-sequencing the genome of RH89-039-16 and PI 225689 to obtain the genome sequence information.

(2) Screening for the InDel markers of the parental materials:

The nucleotide sequence of the StSCI gene and the nucleotide sequence of the StSCI gene linkage are analyzed to screen out that a 538 bp nucleotide sequence is inserted in the promoter region of the StSCI gene.

The inserted nucleotide sequence has the nucleotide sequence represented by SEQ ID NO: 2; and the genetic distance of gene linkage is less than 10 cM.

(3) Designing the InDel molecular markers:

An appropriate first primer pair is designed upstream and downstream of the inserted sequence; an appropriate second primer pair is also designed upstream of the inserted sequence and in the inserted sequence. A first primer pair for amplifying a sequence including the inserted sequence in the promoter region and a second primer pair for amplifying part of the insertion sequence in the promoter region are designed; and the sequences of the two primer pairs are as follows:

```
the first upstream primer 1F:
                                (SEQ ID NO: 7)
5'-CGTCGGATTCAGCAGCAGAGTT-3';

the first downstream primer 1R:
                                (SEQ ID NO: 8)
5'-TCCACATGAGTTGTTTGTTTGGTGTAT-3' the second upstream primer 2F:
                                (SEQ ID NO: 9)
5'-CGTCGGATTCAGCAGCAGAGTT-3';

the second downstream primer 2R:
                                (SEQ ID NO: 10)
5'-AAGCGAATTACAAGCCTGTTTAGATTGAC-3'.
```

(4) Identifying whether the screened molecular markers are usable:

The screened two pairs of InDel molecular markers are identified whether they are identical to the genome sequencing results of RH89-039-16 and PI 225689 parent materials, and the test results show that they are identical. The InDel molecular markers may be used for subsequent identification.

Example 5

A method for identifying whether a diploid potato is self-compatible, including the following steps:
(1) performing hybridization by using the self-compatible diploid potato RH89-039-16 and the self-incompatible diploid potato PI 225689 as the parent materials to obtain the hybrid offspring;
(2) extracting the leaf genome of the hybrid offspring plants when they grow to the seedling stage;
(3) identifying the leaf genome by using the KASP molecular markers obtained by the method of Example 2, if the [T: T] or [T: C] exists at position 58030614 bp in chromosome 12 of the hybrid offspring, then it is self-compatible; otherwise, if [C: C] exists at such a position, then it is self-incompatible. Since the hybrid offspring plant has the same base at the same position in the chromosome of RH89-039-16, it indicates that this offspring plant has obtained the chromosome including the StSCI gene.

Example 6

A method for identifying whether a diploid potato is self-compatible, including the following steps:
(1) performing hybridization by using the self-compatible diploid potato RH89-039-16 and the self-incompatible diploid potato PI 225689 as the parent materials to obtain the hybrid offspring;
(2) extracting the leaf genome of the hybrid offspring plants when they grow to the seedling stage;
(3) identifying the leaf genome by using the InDel molecular markers obtained by the method of Example 3; since the StSCI gene included in RH89-039-16 is heterozygous, and the 11 bp is missing in chromosome 12, two bands of the 97 bp and 108 bp fragments are amplified in RH89-039-16 by the InDel molecular marker primers, while there is only a band of the 108 bp fragment amplified in PI 225689.

Therefore, when the PCR products amplified by InDel molecular marker primers from the diploid potato hybrid offspring are subjected to PAGE electrophoresis, if the resulting band type is consistent with that of RH89-039-16, the hybrid offspring plant is self-compatible; otherwise, if the resulting band type is consistent with that of PI 225689, the hybrid offspring plant is self-incompatible.

Example 7

A method for identifying whether a diploid potato is self-compatible, including the following steps:
(1) performing hybridization by using the self-compatible diploid potato RH89-039-16 and the self-incompatible diploid potato PI 225689 as the parent materials to obtain the hybrid offspring;
(2) extracting the leaf genome of the hybrid offspring plants when they grow to the seedling stage;
(3) identifying the leaf genome by using the two pairs of InDel molecular markers obtained by the method of Example 4; wherein the genomic DNA to be tested is used as a template, the first primer pair (1F and 1R) in Example 4 is used as a group, and the second primer pair (2F and 2R) in Example 4 is used a group, performing PCR amplification reaction separately.

A 20 µl amplification system is used in the PCR reaction: 1 µl of 10-20 ng/µl template DNA, 1 µl of 10 pmol/µl primers F and R respectively, 0.4 µl of 10 mmol/L dNTP mix, 0.3 µl of 0.5U/µL Taq DNA polymerase, 2 µl of 10×PCR reaction buffer, and the rest is water.

PCR reaction conditions are: 94° C. for 5 min; 94° C. for 20 sec, 55° C. for 20 sec, 72° C. for 30 sec, 35 cycles; 72° C. for 10 min.

(4) Detecting the PCR amplification products, i.e., detecting the PCR reaction products by agarose gel electrophoresis. If the size of the fragment amplified by the first primer pair is 500 bp, and there is no any band amplified by the second primer pair, it indicates that the hybrid offspring material is self-incompatible; otherwise, if the size of the fragment amplified by the first primer pair is 500 bp, and a band of 400 bp fragment is amplified by the second primer, it indicates that the hybrid offspring material is heterozygous and self-compatible, since the plant is self-compatible, after self-crossing the offspring of this plant will have a separation of self-compatibility phenotype.

The above descriptions are only preferred examples of this application, and are not intended to limit this application. Any modification, equivalent replacement, etc. made within the spirit and principle of this application shall be covered in the protection scope of this application.

What is claimed is:

1. A method for identifying a self-compatible diploid potato plant or part thereof, comprising:

isolating DNA from a diploid potato plant or part thereof, and using the isolated DNA and primer F comprising SEQ ID NO: 5 and primer R comprising SEQ ID NO: 6 in a PCR reaction;

wherein, a self-compatible diploid potato plant is identified by producing a 97 bp PCR product.

2. The method of claim 1, further comprising:

using PCR and primer 2F comprising SEQ ID No: 9 and primer 2R comprising SEQ ID No: 10, wherein the self-compatible diploid potato plant produces a 428 bp PCR product.

3. The method of claim 2, further comprising:

using PCR and primer 1F comprising SEQ ID No: 7 and primer 1R comprising SEQ ID No: 8, wherein a heterozygous self-compatible plant produces a 500 bp PCR product in addition to the 428 bp PCR product.

4. A method for identifying a self-compatible diploid potato plant or part thereof, comprising:

isolating DNA from a diploid potato plant or part thereof, and using the isolated DNA and primer F comprising SEQ ID NO: 5 and primer R comprising SEQ ID NO: 6 in a PCR reaction;

wherein, the isolated DNA is from a self-compatible diploid potato plant that is an offspring of RH89-039-16 and is identified by producing a 97 bp PCR product.

5. The method of claim 4, further comprising:

using PCR and primer 2F comprising SEQ ID No: 9 and primer 2R comprising SEQ ID No: 10, wherein the self-compatible diploid potato plant produces a 428 bp PCR product.

6. The method of claim 4, further comprising:

using PCR and primer 1F comprising SEQ ID No: 7 and primer 1R comprising SEQ ID No: 8, wherein a heterozygous self-compatible diploid potato plant produces a 500 bp PCR product in addition to the 428 bp PCR product.

* * * * *